United States Patent
Kato et al.

(10) Patent No.: US 9,511,035 B2
(45) Date of Patent: Dec. 6, 2016

(54) JAVA GINGER EXTRACT AND MANUFACTURING METHOD

(71) Applicant: Hosoda SHC Inc., Fukui-shi (JP)

(72) Inventors: Eishin Kato, Fukui (JP); Yoshiyasu Fukuyama, Itano-gun (JP); Miwa Dounoue, Tokushima (JP); Shinya Hosoda, Fukui (JP); Winarno Tohir, Jakarta (ID)

(73) Assignee: Hosoda SHC Inc., Fukui-Shi (JP)

( * ) Notice: Subject to any disclaimer, the term of this patent is extended or adjusted under 35 U.S.C. 154(b) by 43 days.

(21) Appl. No.: 14/234,755

(22) PCT Filed: Aug. 28, 2013

(86) PCT No.: PCT/JP2013/073043
§ 371 (c)(1),
(2) Date: Jan. 24, 2014

(87) PCT Pub. No.: WO2015/029169
PCT Pub. Date: Mar. 5, 2015

(65) Prior Publication Data
US 2015/0216818 A1 Aug. 6, 2015

(51) Int. Cl.
*A61K 9/00* (2006.01)
*A61K 31/09* (2006.01)
*C07C 43/215* (2006.01)
*A61K 31/04* (2006.01)
*A61K 36/9068* (2006.01)
*A61K 9/20* (2006.01)
*A61K 9/48* (2006.01)
*A61K 36/9066* (2006.01)
*A23G 1/48* (2006.01)

(52) U.S. Cl.
CPC .......... *A61K 31/09* (2013.01); *A23G 1/48* (2013.01); *A23K 20/10* (2016.05); *A23K 20/111* (2016.05); *A23K 50/40* (2016.05); *A23K 50/48* (2016.05); *A23L 27/10* (2016.08); *A23L 33/105* (2016.08); *A61K 9/2018* (2013.01); *A61K 9/48* (2013.01); *A61K 9/4858* (2013.01); *A61K 31/04* (2013.01); *A61K 36/9066* (2013.01); *A61K 36/9068* (2013.01); *C07C 43/215* (2013.01); *A23P 10/28* (2016.08); *A23P 10/35* (2016.08); *A23V 2002/00* (2013.01); *A61K 2236/00* (2013.01); *C07C 2101/16* (2013.01)

(58) Field of Classification Search
CPC ........ A23G 1/48; A23K 50/00; A23K 20/00; A61K 36/00; A61K 31/00; A61K 9/00; A23L 33/00; A23L 27/00
See application file for complete search history.

(56) References Cited

FOREIGN PATENT DOCUMENTS

| JP | 08-143454 A | 6/1996 | |
|---|---|---|---|
| JP | 2003-306438 A | 10/2003 | |
| JP | 2003-313116 A | 11/2003 | |
| JP | 2010-090053 A | 4/2010 | |
| WO | WO 2012078798 A1 * | 6/2012 | ........... A23L 1/2128 |

OTHER PUBLICATIONS

Wanauppathamkul. Plaitanoids. The Innovation Development Fund & International Laboratories Corp., Ltd. 2003 26pp.*
Kuroyanagi et al. Further Characterization of the Constituents of a Thai Medicinal Plant, Zingiber cassumunar ROXB. Chem. Pharm. Bull. 1980, 28(1):2948-2959.*
Lu et al. Rapid screening of bioactive components from Zingiber cassumunar using elution-extrusion counter-current chromatography. Journal of Chromatography A, 1181 (2008) 33-44.*

(Continued)

*Primary Examiner* — Robert A Wax
*Assistant Examiner* — Olga V Tcherkasskaya
(74) *Attorney, Agent, or Firm* — Locke Lord LLP

(57) ABSTRACT

The present invention relates to a Java ginger extract which is prepared from Java ginger as a starting material and aimed at a concentrate as an objective (concentrate including solid matter) obtained from a solute. The starting material or the products on any of the steps in which the objective is manufactured from the starting material is heated or exposed to sunlight. In relation to a peak area ratio on high-performance liquid chromatography (HPLC), the peak area ratio (D/M ratio) of a phenyl butenoid dimer represented by the following formula (1) to a monomer represented by the following formula (2) is 0.6 or higher. An intake/dose of the Java ginger extract can be decreased by increasing a content of a phenyl butenoid dimer with an NGF-like action.

[Chemical formula 1]

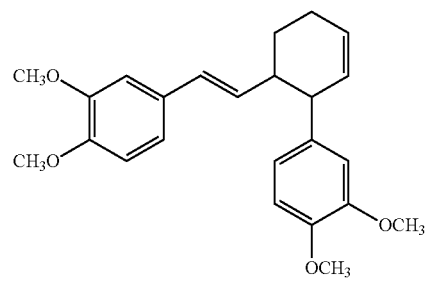

(1)

[Chemical formula 2]

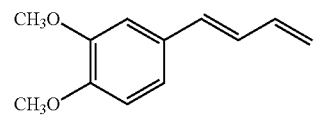

(2)

15 Claims, 3 Drawing Sheets

(56) References Cited

OTHER PUBLICATIONS

Wohlmuth. Phytochemistry and pharmacology of plants from the ginger family, *Zingiberaceae*. PhD thesis, Southern Cross University, Lismore, NSW. 2008.*

Medicinal Food Pharmaceutical Science Handbook (Editors: Isao Kitagawa, Masayuki Yoshikawa), Kondansha Ltd., 2005, pp. 54-55, 122-125, and a cover page.

Megumi Nakai, et al., "Synopsis on 3rd Symposium on Pharmaceutical Food Service," The Pharmaceutial Society of Japan, Division of Natural Medicines, 2009, p. 65 to 67 and a cover page.

Nakamura, Seikou et al, "Structures of New Phenylbutanoids and Nitric Oxide Production Inhibitors from the Rhizomes of *Zingiber cassumunar*," Chemical & Pharmaceutical Bulletin, 2009, 57(11), pp. 1267-1272.

Tuntiwachwuttikul, Pittaya et al, "Syntheses of some constituents of *Zingiber cassumunar*," Australian Journal of Chemistry, 1980, 33 (4), pp. 913-916.

Mori, Iwao et al, "Isolation and structure of alflabene from *Alpinia flabellata* Ridl," Tetrahedron Letters, 1978, (26), pp. 2297-2298.

Matsui, Nobuaki et al, "Phenylbutenoid dimers isolated from *Zingiber purpureum* exert neurotrophic effects on cultured neurons and enhance hippocampal neurogenesis in olfactory bulbectomized mice," Neuroscience Letters, 2012, 513(1), pp. 72-77.

International Search Report dated Sep. 24, 2013, issued for PCT/JP2013/073043.

Biochemistry Dictionary, 3rd Edition (Editors: Kazutomo Imahori, Tamio Yamakawa), Tokyo Kagaku Dojin, 1998, pp .710-713, cover page and partial English translation.

\* cited by examiner (min.)
D/M ratio=0

(min.)
D/M ratio=0.24

JAVA GINGER EXTRACT AND MANUFACTURING METHOD

TECHNICAL FIELD

The present invention relates to a Java ginger extract with a higher content of a phenyl butenoid dimer which is contained in Java ginger as an active ingredient and has neurotrophic factor-like actions, and to a manufacturing method thereof.

BACKGROUND ART

The phenyl butenoid dimer has an NGF-like action (one of the actions of the neurotrophic factor) effective as a prophylaxis and/or treatment of neurogenic diseases such as brain ischemia, Alzheimer's disease, Parkinson's disease and Huntington's disease.

Herein, "NGF" means an abbreviation for "Nerve growth factor" which is a cytokine peptide factor showing differentiation/growth activities of nerve tissues ("IWANAMI's BIOLOGY DICTIONARY, $4^{th}$ Edition," 1998, Iwanami Shoten, Publishers).

Senile dementia (mental deterioration) is becoming a more common social problem with the rapid aging of society. As types of senile dementia, Alzheimer's disease and cerebrovascular dementia are known.

For Alzheimer's disease, treatments by acetylcholinesterase inhibitors or the like have been tried, but are limited, and there is no effective therapy yet because of unclear pathogeny and advanced disease. Thus, development of an NGF production promoter or an NGF-like action substance is strongly desired in order to prevent and treat dementia, because the NGF is needed for growth of neurocytes, promotion of neurite formation/extension, maintenance of activity and protection of neuronal cell death.

In addition, BIOCHEMISTRY DICTIONARY, $3^{rd}$ Edition (Editors: Kazutomo Imahori, Tamio Yamakawa), p. 711, Tokyo Kagaku Dojin (1998) (NonPatent Document 1) discloses that since this NGF is a peptide factor which acts on cholinergic neurons of Meynert's nucleus basalis in a basal forebrain as a neuron group which experiences remarkable loss particularly with Alzheimer's disease, its direct application for treatment of Alzheimer's disease is being tried. However, the NGF cannot pass through the blood-brain barrier as it has a high molecular weight (polypeptide), and hence it is intraventricularly administered, resulting in many problems.

Thus, the present inventors previously found that the phenyl butenoid dimer (substituted cyclohexene) which is a solvent-extracted concentrate from an Indonesian zingiberaceous plant (Java ginger) showed an NGF-like action as one action of neurotrophic factor-like actions, and proposed a healthy composition containing an extract which is a concentrate of a liquid extracted from Java ginger in Japanese patent publication No. 2010-90053 A (Patent Document 1).

As components of the zingiberaceous plant commonly used in Japan, gingerol, curcumin, curcumene, etc., are known as disclosed in Medicinal Food Pharmaceutical Science Handbook (Editors: Isao Kitagawa, Masayuki Yoshikawa), pp. 54 and 122, Kodansha Ltd. (2005)(Non Patent Document 2), but the phenyl butenoid dimer (1) and monomer (2) respectively represented by the following chemical formulas have not been recognized.

[Chemical formula 1]

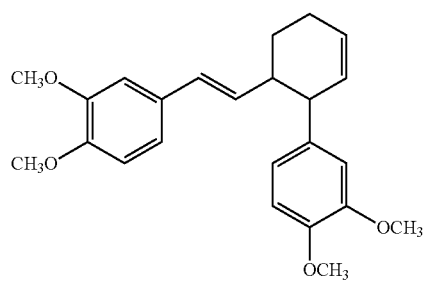

[Chemical formula 2]

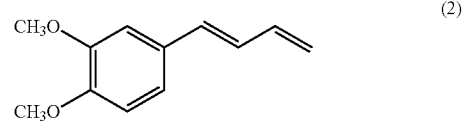

Meanwhile, in the Java ginger, two components, the above-mentioned monomer and dimer have been recognized as disclosed in Synopsis on $3^{rd}$ Symposium on Pharmaceutical Food Science (Megumi Nakai, et al.), p. 65 to 67, The Pharmaceutical Society of Japan, Division of Natural Medicines (2009) (Non Patent Document 3).

Since a content of the phenyl butenoid dimer in the solvent-extracted Java ginger extract is extremely low compared to that of the monomer showing no NGF-like action, an intake of the extract should be increased to exert the NGF-like action at an effective level.

In addition, Japanese patent publication No. 2003-313116 A (Patent Document 2) discloses that the phenyl butenoid dimer has platelet-activating factor antagonism and tyrosinase activity-inhibiting action. Furthermore, Japanese patent publication No. 2003-306438 A (Patent Document 3) discloses that the phenyl butenoid dimer has chemokine expression-inhibiting action.

However, all of the Patent Documents 1 to 3 and the Non Patent Document 3 do not disclose nor suggest a trial to increase the content of the phenyl butenoid dimer in the Java ginger extract.

DISCLOSURE OF THE INVENTION

Problems to be Solved by the Invention

In light of the above description, the object of the present invention is to provide a Java ginger extract which allows its intake/dose to decrease by increasing the content of the phenyl butenoid dimer with the NGF-like action and is useful as a prophylaxis and/or treatment of neurogenic diseases such as brain ischemia, Alzheimer's disease, Parkinson's disease and Huntington's disease.

Means for Solving the Problems

As a result of intense study for solving the problems, the present inventors found that a phenyl butenoid monomer was transformed into the phenyl butenoid dimer by heating the solute, and completed the present invention.

That is, the present invention is contained in the Java ginger extract having a new composition in which the content of the phenyl butenoid dimer with the NGF-like action is remarkably increased by thermally transforming a phenyl butenoid monomer in the Java ginger extract (see "Table 1," Examples 3 to 5 described below), Effects of the Invention According to the present invention, a Java ginger extract in which the content of the phenyl butenoid dimer with the NGF-like action is increased and its specific odor is reduced by heating is prepared, thereby a usage of the extract is decreased and the odor is reduced, so that applications of the preparation are expanded, and thus it can widely contribute to prophylaxis and/or treatment of neurogenic diseases such as brain ischemia, Alzheimer's disease, Parkinson's disease, Huntington's disease, etc., by neuronal process extension and protection of neuronal cell death.

Thus, the Java ginger extract which is made of safe Java ginger widely eaten in Southeast Asia and has a higher content of the phenyl butenoid dimer can contribute to prophylaxis or treatment of neurogenic diseases in daily life. The phenyl butenoid dimer induces differentiation of a rat adrenal medullary pheochromocytoma (PC12 cell) as is the case with the NGF and shows a process extension activity, thereby holds the possibility to provide effects on hair growth by acting on hair root cells, and therefore it is useful for improvement and suppression of balding.

BEST MODE FOR CARRYING OUT THE INVENTION

Figure 1:
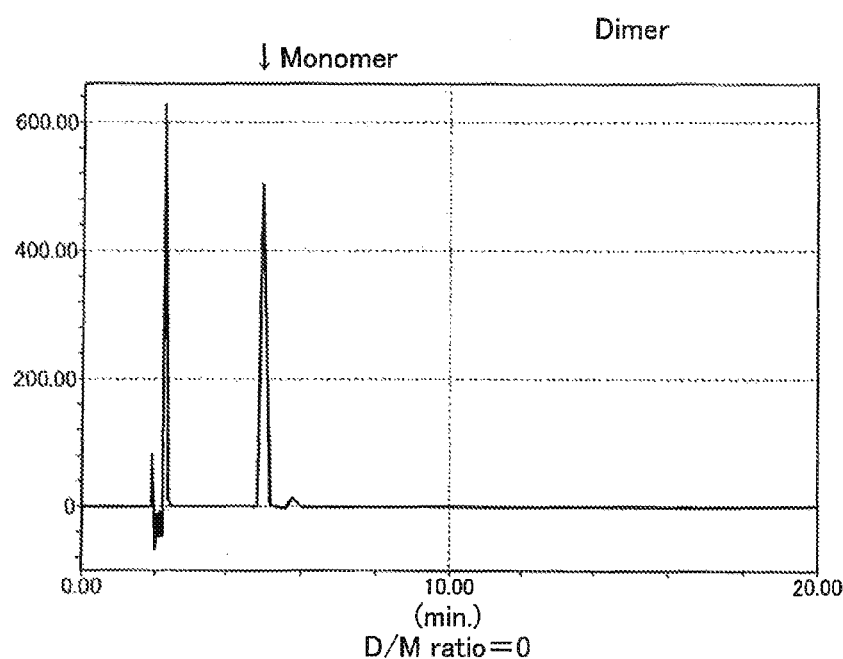
FIG. 1 represents an HPLC chromatogram of the phenyl butenoid monomer in a solution of ethanol.

Hereinafter, embodiments of the present invention will be explained.

The phenyl butenoid dimer represented by the following formula (1) in the present invention is a compound in which an absolute configuration at position 3 in the cyclohexene ring is R- or S-configuration, an absolute configuration at position 4 is R- or S-configuration, and steric configurations at positions 3 and 4 are trans- or cis-configuration.

[Chemical formula 3]

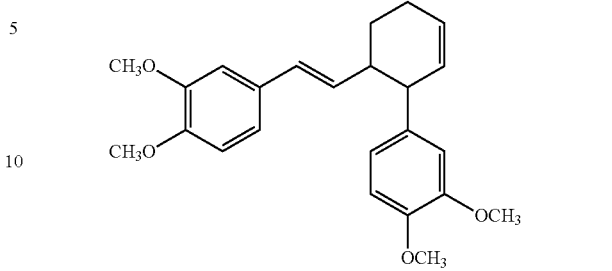

(1)

The Java ginger in the present invention is a plant which belongs to the Zingiberaceae, genus *Zingiber* and grows in tropical and subtropic regions. Among the Java gingers, Bangle (also known as Bengle, scientific name: *Zingiber purpureum* Roxb, Indonesian name: Bangle, Bengle) and/or Zedoary (scientific name: *Zingiber cassumunar* Roxb., Indonesian name: Bangle, Bengle) are widely grown in Southeast Asia and eaten as jamu (folk medicine). Also they are used as spices.

Although whole grass can be used in the present invention, it is preferable to use rhizome from the standpoint of yield, and the ginger may be used in both dried and undried conditions.

Heating treatment means that an atmosphere temperature is set to 55° C. or higher by a heat source such as electricity, gas, steam and far-infrared rays using an incubator, a temperature/pressure-adjustable heating tank or the like which can adjust the temperature to be desirable.

To obtain an extract, undried and dried Java ginger is used as a feed in an unchanged form or a size-reduced form, soaked in a solvent, and the Java ginger as a solid raffinate is filtered out.

The size reduction of the Java ginger is carried out by means of cut/slice, crush, grinding or the like. Specifically, a sliced article of an undried/dried Java ginger, a paste article obtained by grinding the undried Java ginger by a wet grinder, a freeze-dried article thereof and a freeze-dried ground article thereof, or crushed/ground articles of the dried Java ginger can be exemplified.

The above-described solvent is not particularly limited, as long as the solvent can dissolve (extract) the phenyl butenoid monomer and the phenyl butenoid dimer, Typically, hydrophilic solvents such as the below-exemplified alcohols, ethers, organic acids and amines can be used. Also, a mixed solvent in which hydrophobic solvents such as the below-exemplified hydrocarbons and halogenated hydrocarbons are optionally mixed can be used. Evaporation of the solvent is enhanced, so that the drying process can be enhanced. One or a plurality of these solvents can be combined, and water can be optionally added.

Hydrophilic Solvents

Alcohols: methanol, ethanol, 1-propanol, 2-propanol, 1-butanol, ethylene glycol, propylene glycol, glycerol.

Ethers: diethyl ether, cellosolve, dioxane, tetrahydrofuran.

Esters: methyl acetate, ethyl acetate, cellosolve acetate.

Ketones: acetone, methyl ethyl ketone.

Organic acids: glacial acetic acid, propionic acid.

Amines: 2-aminoethanol, pyridine, monomethanolamine.

Hydrophobic Solvents

Hydrocarbons: hexane, cyclohexane, heptane, benzene, toluene, xylene.

Halogenated hydrocarbons: methylene chloride, chloroform, 1,2-dichloroethane, dichioroethylene, trichloroethylene.

The extract means a solid (including paste) concentrate obtained from a solute by evaporating a solvent under a reduced pressure or ordinary pressure.

For the Java ginger extract of the present invention, the Diels-Alder reaction in which a dimer by conjugation between two molecules at a diene moiety in the monomer represented by the following chemical formula (2) is produced is focused.

[Chemical formula 4]

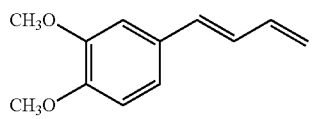

(2)

In order to promote the Diels-Alder reaction at a practical rate, the reaction is carried out by heating or sunlight exposure. Sunlight is a natural energy and contributes to energy saving. Herein, the sunlight exposure also includes an exposure manner in which mainly a heat ray (infrared ray) is used, as in a hothouse.

In a case of heating, temperature is preferably 55 to 160° C., more preferably 85 to 140° C., even more preferably 95 to 130° C. At a low temperature, the reaction rate is low, and at high temperature, a polymerization reaction is likely to be accompanied. The temperature is arbitrarily set in consideration of energy/production efficiency. This polymerization reaction can be somewhat reduced by addition of an antioxidant such as tocopherol, ubiquinol, ascorbic acid, catechin and hydroquinone.

In the case of the sunlight, natural energy can be used and it can be applied to mass production.

The exposure time of the sunlight is preferably within 8 hours, and if it exceeds that time, a side reaction (further polymerization reaction) is likely to occur.

The heating and sunlight exposure may be conducted under any of an ordinary pressure, an increased pressure and a reduced pressure. In addition, the atmosphere in heating and sunlight exposure may be any of air, nitrogen, rare gas or carbon dioxide, and this is arbitrarily selected.

A chromatogram in high-performance liquid chromatography (hereinafter, abbreviated to HPLC) can be obtained by detection at a flow rate of 1 mL/min. and at 254 nm, using an octadecyl silica (ODS) column with 80% methanol for a mobile phase. A ratio of a peak area of the dimer to a peak area of the monomer (2) on the chromatogram (D/M ratio) is adjusted to a non-conventional composition, i.e., a D/M ratio: 0.6 or higher by promoting the Diels-Alder reaction through heating and/or sunlight exposure (i.e., the monomer is decreased and the dimer is increased). Desirably, the ratio is adjusted to 1.0 or higher, more desirably 5.0 or higher. When heating and/or sunlight exposure are conducted after extraction, the ratio is adjusted to be more than fourfold, more desirably more than twentyfold higher than the D/M ratio of the solute.

The manufacturing method for increasing the content of the phenyl butenoid dimer is as mentioned below. The Java ginger as the raw material may be either undried or dried, and may be used in any form of a rhizome as it is, sliced or crushed powder.

(1) Non-heated Java ginger is heated to 55 to 160° C., then a solvent is added so as to soak it therein, and the Java ginger is removed to obtain a solute. The solvent is distilled away from the solute to obtain the Java ginger extract in a form of concentrate.

(2) The non-heated Java ginger is heated while being soaked in the solvent in the same way as (1), then Java ginger is removed to obtain a solute. The solvent is distilled away from the solute to obtain the Java ginger extract in a form of concentrate.

(3) The non-heated Java ginger is soaked in the solvent, and a solute obtained by removing the Java ginger is heated in the same way as (1), then the solvent is distilled away to obtain the Java ginger extract in a form of concentrate.

(4) The non-heated Java ginger is soaked in the solvent, and the Java ginger is removed, then the concentrate obtained by distilling away the solvent in the solute is heated to 55 to 160° C. in the same way as (1) to obtain the Java ginger extract.

(5) The non-heated sliced (for increasing the area exposed to sunlight) Java ginger is exposed to sunlight, then soaked in the solvent, and the solvent is distilled away from a solute obtained by removing the Java ginger to obtain the Java ginger extract in a form of concentrate.

(6) The non-heated Java ginger is soaked in the solvent, and a solute obtained by removing the Java ginger is exposed to sunlight, then the solvent is distilled away to obtain the Java ginger extract in a form of concentrate.

The D/M ratio of the Java ginger extract obtained in this way is remarkably higher than that of the conventional extract obtained by solvent extraction. That is, the D/M ratio of the Java ginger extract of the present invention is preferably 0.6 or higher, additionally 1.0 or higher, even still 5.0 or higher, as shown in the Examples described below. Thus, since the Java ginger extract having a high content of the phenyl butenoid dimer allows the intake as an extract to decrease, and therefore the application as a food/drink product, a health food, a preventive agent and a therapeutic agent as a prophylaxis and/or treatment of neurogenic diseases is expanded.

A diet (foods and drinks) containing or comprising the Java ginger extract related to the present invention has the phenyl butenoid dimer at a high percentage not found conventionally. Thus, the diet of the present invention can be designated as a health food, furthermore a food for specified health use, and manufactured by blending with various components which are conventionally used for foods as required.

The form of the diet may include any form for diet such as a powdery food (including granules), a solid food, a cream or jam-like semiliquid food, a gel-like food and a beverage. Among them, the powdery food is preferable because of its excellent handling property and portability.

Preparations such as powder, granule, tablet, capsule and tonic drink; liquid products such as powdery soft drink, soft drink, juice, coffee, tea, liqueur, milk, whey beverage, lactic acid bacteria beverage and yoghurt; solid products such as candy, caramel candy, chewing gum, chocolate, gummy candy, ice cream, pudding, egg product, adzuki-bean jelly, soft adzuki-bean jelly, okaki, rice cake, rice dumpling, rice cracker, crape, okonomiyaki, bread, cookie, noodle, hamburger, water-kneaded product, tempura, fermented food, and seasoned powder for sprinkling over rice, which comprise any substrate in common use, are exemplified.

The diet in these forms may be added with the extracted matter of the following crude drug/health tea (including extract) or the like.

These may include angelica keiskei, hydrangea tea, gynosteme, aloe, ginkgo leaf, oolong tea, turmeric, Quercus salicina, Siberian ginseng, fleawort, Glechoma Hederacea, persimmon, Matricaria recutina, camomile, quince, garcinia cambogia, Cassia mimosoides, chrysanthemum flower, gardenia, gnetum, mulberry, Lycium chinense, laurel, red tea, Taxus mairei, Russian comfrey, seaweed, cherry blossom, saffron, Chinese mushroom, perilla, ginger, field horsetail, kaffir lime, grassy-leaved sweet flag, bidens, swertia herb, buckwheat, tamarind, Japanese angelica tree, dandelion, chicory, du zhong, sword bean, elder, Japanese privet, Job's tears, swordweed, grape, pine needle, yerba mate, barley tea, mangosteen, Nikko maple, melinjo, eucalyptus, mugwort, Luo Han Guo, green tea, rooibos, shelf fungus, galangal, Gymnema sylvestre, guava leaf, geranium herb, brown rice, burdock, houttuynia cordata, banaba, loquat leaf, safflower, etc.

Optionally, a sugar alcohol such as erythritol, sorbitol, maltitol and xylitol, as well as glucose, fructose, sucrose, lactose, dextrin and the like may be blended for preparation.

In addition, the preventive agent and the therapeutic agent are a preparation which consist mainly of the phenyl butenoid dimer and are prepared as a solid agent by adding any auxiliary agent, vehicle or the like as required, or prepared as a liquid agent by optionally adding water, an organic solvent or the like.

When the Java ginger extract of the present invention is used as a food/drink product for improvement or prophylaxis of neurogenic diseases or the like, the compounding ratio of the Java ginger extract ranges within 0.01 to 90%, preferably 0.05 to 80% on a dry weight basis in consideration of flavor and color tone as the food/drink product.

To the Java ginger extract of the present invention, a sweetener (1), an acidulant (2), an antioxidant (3), an improving agent (4), a starch adhesive (thickener, stabilizer, gelling agent) (5), a nutrient enrichment (6) and a seasoning (7) can be added according to a kind of the product. In addition, materials used as common raw materials for foods and drinks such as calcium salts, an emulsifier, a colorant, an expansion agent, a flavoring agent and a preservative can be optionally added.

(1) glucose, fructose, sucrose, maltose, sorbitol, stevioside, glycyrrhizin, aspartame, rubusoside, corn syrup, lactose.

(2) citric acid, tartaric acid, malic acid, succinic acid, lactic acid.

(3) L-ascorbic acid, dl-α-tocopherol, sodium erythorbate.

(4) glycerin, propylene glycol.

(5) gum arabic, carrageenan, casein, gelatin, pectin, agar.

(6) vitamins, nicotinamide, calcium pantothenate, eicosapentaenoic acid (EPA), docosahexaenoic acid (DHA).

(7) amino acids, inosinic acids.

When the Java ginger extract of the present invention is used as an oral agent for improvement and prophylaxis or treatment of neurogenic diseases, its dosage (dose of administration) will vary depending upon the purpose of the administration, condition of a consumer (gender, age, body weight, degree of obesity, degree of total health, etc.). Typically, as a daily dosage, the Java ginger extract can be administered in the range of 1 to 200 mg/kg body weight on a dry weight basis. Since the Java ginger as a raw material is regularly eaten, there is no problem with a dosage of higher than 200 mg/kg body weight. In addition, it can be applied to animals in the same manner. The Java ginger can be used as not only an oral agent but also as a dermatological agent.

In addition, when the extract is used as an animal feed, it may be made in a form such as powder (including granules), paste, capsule or syrup, a solid form, a gelled form and a liquid form (solution, suspension, emulsion) by optionally adding the above-mentioned various components.

The animal feed includes pet food such as livestock feed, cat food, dog food and rabbit food.

EXAMPLES

Hereinafter, the present invention will be detailed by Examples, Comparative Examples, Tests, Composition Example, but is not limited to these Examples.

In addition, the ratio of the phenyl butenoid dimer to the phenyl butenoid monomer (hereinafter, called "D/M ratio") in the following Examples, Comparative Examples, Tests, etc., was determined from the peak area ratio of the dimer to monomer on the chromatogram measured using HPLC (high performance liquid chromatography).

Standard samples of phenyl butenoid monomer and dimers in each example were prepared by the following method for use.

"1.5 L of a solute prepared in the same way as in the following Example 4 was concentrated under reduced pressure to obtain 36 g of a brown paste-like concentrate. This concentrate was separated by silica gel column chromatography (silica gel: 400 g, eluent: n-hexane/ethyl acetate) to obtain 3.38 g of monomer as a nearly-colorless oily substance with viscosity and 1.2 g of dimer (mixture of trans and cis forms). This dimer was separated again by silica gel column chromatography (silica gel: 200 g, eluent: methylene chloride/n-hexane/ethyl acetate) to obtain 0.3 g of trans form and 0.3 g of cis form respectively in a form of needle-like crystal. Their melting points were 80 to 81° C. and 98 to 99° C. respectively. This isolated monomer (M) as well as trans- and cis-dimers was used as the standard sample for HPLC."

(1) EXAMPLES

Hereinafter, each example of manufacturing the extract (Example) will be explained. In addition, the solute prepared in Example 3 was partly used in Example 3, and the remaining part was used in Example 5 and Test 3.

Example 1

Sixty four grams of rhizome of a washed Java ginger was maintained as it was at 110° C. for 12 hours, and cooled down, then sliced (thickness: about 0.5 mm) by a slicer, soaked in 250 mL of 90% ethanol at room temperature for 2 days, and filtered through a filter paper to obtain a solute, which was concentrated and solidified by drying to obtain 2.1 g of brown resinous Java ginger extract having a reduced specific odor.

The D/M ratio in this Java ginger extract was 6.1.

Example 2

Fifty grams of the Java ginger sliced (thickness: about 0.5 mm) by a slicer was heated at 125° C. for 8 hours, and cooled down, then soaked in 250 mL of 90% ethanol at room temperature for 2 days, and filtered through a filter paper to obtain a solute, which was concentrated and solidified by drying to obtain 1.7 g of brown resinous Java ginger extract having a reduced specific odor.

The D/M ratio in this Java ginger extract was 11.2.

Example 3

Two kilograms of the Java ginger sliced (thickness: about 0.5 mm) by a slicer was soaked in 8 L of 95% ethanol at room temperature for 2 days, and filtered through a filter fabric to obtain 6.2 L of yellow solute. 100 mL of this solute was put in a 300 mL conical flask, and left under sunlight for 8 hours, then concentrated and solidified by drying to obtain 1 g of brown resinous Java ginger extract having a reduced specific odor.

The D/M ratio in the Java ginger extract was 0.65, which was 4.3 times higher than the D/M ratio of 0.15 in the solute.

Example 4

After the ginger was sliced (thickness: about 3 mm) by a knife, 500 g of the Java ginger dried by ventilation (not by heating) was soaked in 2.5 L of 70% ethanol for 3 days, and filtered through a filter fabric to obtain 2 L of yellow solute. 200 mL of the solute was maintained at 110° C. for 24 hours, and cooled down, then concentrated and solidified by drying to obtain 4.5 g of brown resinous Java ginger extract having a reduced specific odor.

The D/M ratio in the Java ginger extract was 2.10, which was 8.4 times higher than the D/M ratio of 0.25 in the solute.

Example 5

Six liters of the solute prepared in Example 3 was concentrated under reduced pressure (normal temperature) to obtain 68 g of brown paste-like concentrate having a specific odor. 55 g of the concentrate was maintained at 120° C. for 16 hours to obtain a resinous Java ginger extract having a reduced specific odor.

The D/M ratio in the Java ginger extract was 11.3, which was 75 times higher than the D/M ratio of 0.15 in the solute in Example 3.

Example 6

One kilogram of Java ginger sliced (thickness: about 1 mm) by a knife was dried in the sun (exposed to sunlight for 8 hours) to obtain 274 g of a dry matter. The dry matter was soaked in 1.4 L of 70% ethanol for 3 days, then filtered through a filter fabric, and this filtrate was concentrated and solidified by drying to obtain 26 g of brown resinous Java ginger extract having a reduced specific odor. The D/M ratio in the Java ginger extract was 1.02.

Example 7

Thirty grams of Java ginger sliced (thickness: about 0.5 mm) by a slicer was soaked in 130 mL of dioxane, heated at 105° C. for 20 hours, and cooled down, then the solute obtained by filtration through a filter paper was concentrated and solidified by drying to obtain 1.1 g of brown resinous Java ginger extract having a reduced specific odor. The D/M ratio in the Java ginger extract was 1.47.

Example 8

Four hundreds grams of the Java ginger which was sliced (thickness: about 3 mm) by a knife and then heated by hot air at 100° C. for 12 hours was soaked in 2 L of 70% ethanol at room temperature for 3 days and filtered through a filter fabric, then this filtrate was concentrated and solidified by drying to obtain 41 g of brown resinous Java ginger extract having a reduced specific odor. The D/M ratio in the Java ginger extract was 6.64.

Example 9

Ten grams of Java ginger sliced by a knife was soaked in 50 mL of 100% methanol at room temperature for 3 days and filtered through a filter paper to obtain 46 mL of yellow solute, 5 mL of this solute was incubated under a nitrogen atmosphere at 60° C. for 24 hours, and cooled, then concentrated and solidified by drying to obtain 25 mg of brown resinous Java ginger extract having a reduced specific odor. The D/M ratio in the Java ginger extract was 0.62, which was 2.3 times higher than the D/M ratio of 0.27 in the solute.

Comparative Example 1

Fifty grams of Java ginger sliced (thickness: about 0.5 mm) by a slicer was soaked in 250 mL of 90% ethanol at room temperature for 2 days, filtered through a filter paper to obtain a solute, which was concentrated and solidified by drying to obtain 1.7 g of brown resinous Java ginger extract having a specific odor. The D/M ratio in the extract was 0.14.

The manufacturing conditions/measurement results of the Examples/Comparative Examples are summarized in the following Table 1. The table suggests that the heat condition at high temperature has a higher dimer yield (Example 2 relative to Example 1). In relation to subjects for exposure to sunlight, it is suggested that the raw material has a higher dimer yield than that of the solute (Example 6 relative to Example 3).

TABLE 1

|  | Raw material | Condition on extraction | Subject for heating | Heat condition * | Subject for exposure to sunlight | Time of exposure | D/M ratio |
|---|---|---|---|---|---|---|---|
| Example 1 | Rhizome | 90% EtOH Room temperature x2 d | Raw material | 110° C. X12 h | — | — | 6.1 |
| Example 2 | Slice | 90% EtOH Room temperature x2 d | Raw material | 125° C. x18 h | — | — | 11.2 |

TABLE 1-continued

| | Raw material | Condition on extraction | Subject for heating | Heat condition * | Subject for exposure to sunlight | Time of exposure | D/M ratio |
|---|---|---|---|---|---|---|---|
| Example 3 | Slice | 95% EtOH Room temperature x2 d | — | — | Solute | Mostly sunny in summer 8 h | 0.65 (4.3 times) ** |
| Example 4 | Slice | 70% EtOH Room temperature x3 d | Solute | 110° C. x24 h | — | — | 2.1 (8.4 times) ** |
| Example 5 | Slice | 95% EtOH Room temperature x2 d | (Paste-like) Concentrate | 120° C. x16 h | — | — | 11.3 (75 times) ** |
| Example 6 | Slice | 70% EtOH Room temperature x3 d | — | — | Raw material | Mostly sunny in summer 8 h | 1.02 |
| Example 7 | Slice | Dioxan 105° C. x20 h | Soaking solution | 105° C. x20 h | — | — | 1.47 |
| Example 8 | Slice | 70% EtOH Room temperature x3 d | Raw material | 100° C. (Hot air) x12 h | — | — | 6.64 |
| Example 9 | Slice | 100% MeOH Room temperature X3 d | Solute | 60° C. x24 h | — | — | 0.62 |
| Comparative Example 1 | Slice | 90% EtOH Room temperature x2 d | — | — | — | — | 0.14 |

\* All examples are in incubators except for Examples 3 and 6.
\*\* Numbers in brackets are a multiplying factor to the D/M ratio in the solute.

(2) TESTS

Hereinafter, tests in which heating temperature and influence of sunlight in transformation reaction from the monomer to the dimer were examined will be explained.

<Test 1 (Thermal Reaction of the Monomer)>
A liquid in which 10 mg of monomer isolated in preparation of the standard sample for chromatography was dissolved in 1 mL of 70% ethanol was prepared and put in four test tubes, and these were heated at 90° C., 100° C., 110° C. and 120° C. respectively for 6 hours. Quantification was conducted by high-performance liquid chromatography (HPLC) under the above-mentioned conditions, and the calculated D/M concentration ratios were 0.14, 0.16, 0.19 and 0.24 respectively. From this result, it was confirmed that the greater transformation to the dimer occurred by the heating (reaction) at higher temperature to give the high D/M ratio.

Figure 2:
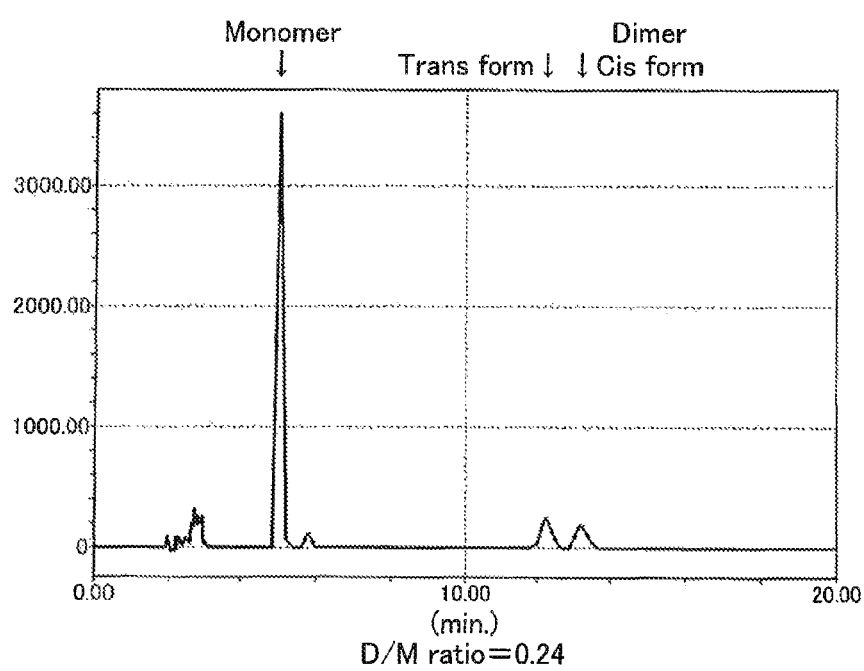
FIG. 2 represents an HPLC chromatogram of a resulting product obtained by heating the phenyl butenoid monomer in the solution of ethanol at 120° C.×6 h in Test 1.

In addition, FIG. 1 shows an HPLC chromatogram of the phenyl butenoid monomer (before heating) in the ethanol solution, and FIG. 2 shows an HPLC chromatogram of the resulting product obtained by heating the ethanole solution at 120° C.x6 h.

Figure 3:
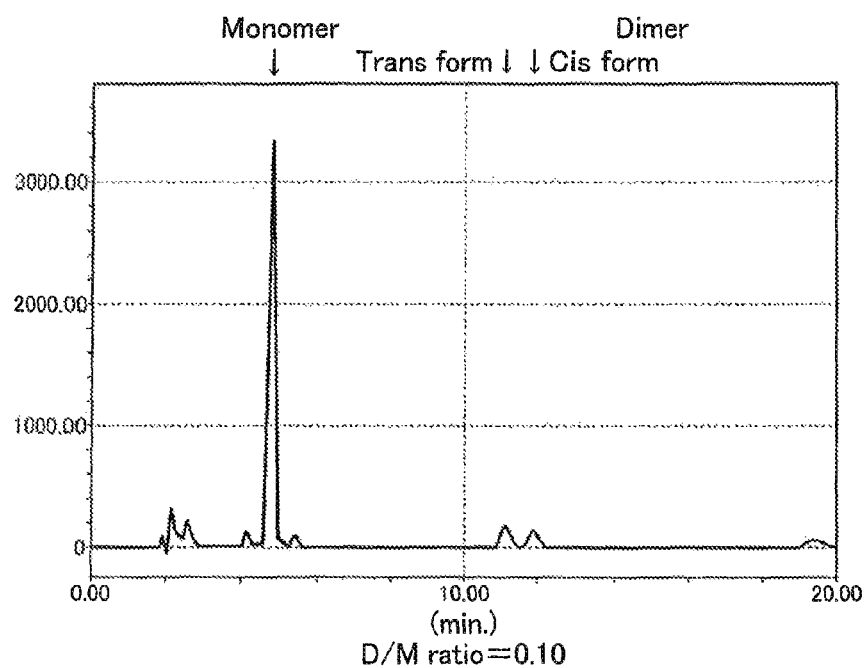
FIG. 3 represents an HPLC chromatogram of a resulting product obtained by exposing the phenyl butenoid monomer in the solution of ethanol to sunlight for 2 hours in Test 2.

<Test 2 (Reaction of the Monomer Under Sunlight)>
A solution dissolved 10 mg of monomer isolated in the same way as Test 1 in 2 mL of 70% ethanol was prepared and put in a test tube, exposed to sunlight for two hours, quantified in the same way as Test 1, and the calculated concentration ratio of D/M ratio was 0.10. This result indicates that the monomer was transformed to the dimer by sunlight. In addition, FIG. 3 shows an HPLC chromatogram of the resulting product obtained by the above-mentioned treatment.

<Test 3 (Thermal Reaction of the Solute)>
One milliliter of the solute in Example 3 was put in 7 test tubes, and these were heated at 80° C., 90° C., 100° C., 110° C., 120° C., 130° C. and 140° C. respectively for 6 hours, quantified in the same way as Example 1, and the calculated DM concentration ratios were 0.21, 0.24, 0.26, 0.29, 0.34, 0.41 and 0.53 respectively.

Figure 4:
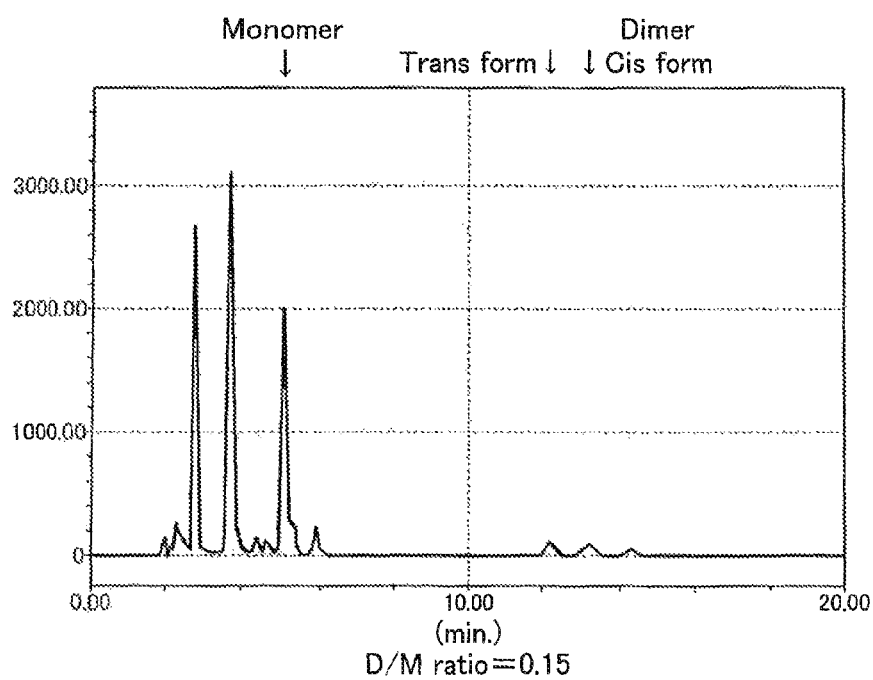
FIG. 4 represents an HPLC chromatogram of the ethanole solute before heating in Example 3.
Figure 5:
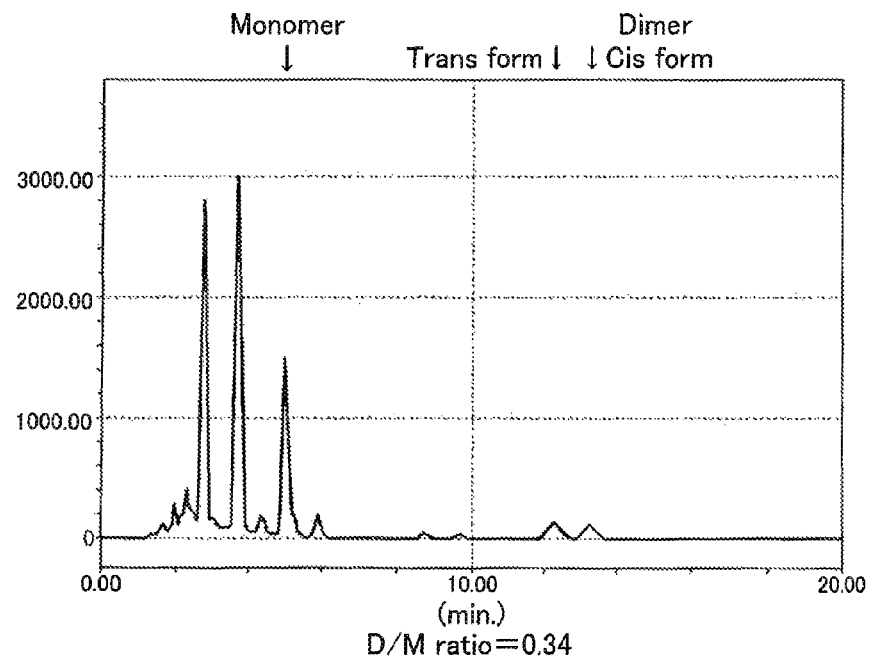
FIG. 5 represents an HPLC chromatogram of the resulting product in Test 3 obtained by heating the ethanole solute prepared in Example 3 at 120° C. for 6 hours

As is the case with Test 1, this result indicated that, as the heating (reaction) temperature increased, the concentration of the dimer increased compared to that in the solute before heating, meanwhile the monomer concentration decreased. Their D/M ratios were 1.4, 1.6, 1.7, 1.9, 2.3, 2.7, 3.5 times higher respectively than the D/M ratio of 0.15 in the solute of Example 3, This test result suggests that the polymerization is suppressed and the yield of the dimer is relatively increased in the Diels-Alder reaction at up to around 160° C. in the present invention. In addition, FIG. 4 shows an HPLC chromatogram of the solute (before heating) in Example 3, and FIG. 5 shows an HPLC chromatogram of the resulting product obtained by heating the ethanole solution at 120° C.x6 h.

<Test 4 (Photoreaction of the Solute)>
One milliliter of the solute prepared in Example 3 was exposed to sunlight for 2 hours and quantified in the same way as Test 1, and the calculated D/M concentration ratio was 0.19. The D/M ratio was 1.3 times higher than that of 0.15 in the solute of Example 3.

Figure 6:
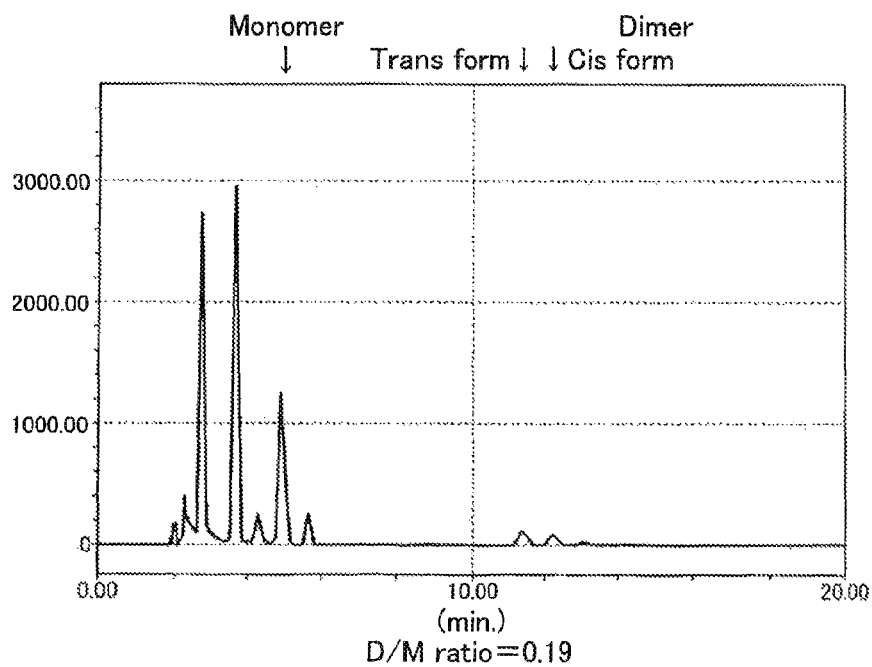
FIG. 6 represents an HPLC chromatogram of the resulting product in Test 4 obtained by exposing the ethanole solute in Example 3 to sunlight for 2 hours.

From this result, it was confirmed that the concentration of the dimer increased compared to that before exposure to sunlight as is the case with Test 2, and the Diels-Alder reaction by which the monomer was dimerized under a brief exposure to sunlight was enhanced. In addition, FIG. 6 shows an HPLC chromatogram of the resulting product obtained by the above-mentioned treatment.

(3) COMPOSITION EXAMPLE

Hereinafter, an example for a composition which is a powder which facilitates productization using the extract of the present invention as a raw material will be explained.

Composition Example 1

Manufacture of the Powder

To a solution in which 20 g of the Java ginger extract prepared in Example 5 was dissolved in 30 mL of ethanol, 60 g of cornstarch (carbohydrate) was added, mixed and then dried to obtain 78.9 g of a powder.

(4) PRODUCT EXAMPLES

Hereinafter, examples (applications) of various products will be explained.

Product Example 1

Chocolate

One part of the powder in Composition Example 1, 220 parts of chocolate, 75 parts of sucrose, 100 parts of cacao butter and 100 parts of whole milk powder were blended to manufacture a chocolate. The blended Java ginger extract did not affect the flavor and color of the chocolate and the taste was good.

Product Example 2

Cookie

One part of the powder in Composition Example 1, 2.3 parts of soft flour, 1.6 parts of whole egg, 1.9 parts of margarine, 2.5 parts of superfine sugar, 0.02 part of baking powder and 0.73 part of water were blended to manufacture a cookie. This cookie had a fine flavor and the taste was good.

Product Example 3

Solid Dog Food

One part of the powder in Composition Example 1, 2.4 parts of meat meal, 0.35 part of chicken extract, 0.3 part of vegetable oil, 1.2 parts of carbohydrate, 0.03 part of calcium carbonate, 0.01 part of salt, 0.05 part of complexed vitamin preparation and 0.6 part of water were blended to manufacture a dog food.

Product Example 4

Tablet

Ten grams of powder in Composition Example 1, 20 g of lactose and 0.1 g of magnesium stearate were mixed, and the mixture was compressed by a single punch tableting to manufacture a tablet having a diameter of 8 mm and a weight of 200 mg.

Product Example 5

Seamless Capsule

To 20 g of the Java ginger extract in Example 5, 2 mL of corn oil was added, mixed while heating to give fluidity, and then filled with a viscous liquid mixed with 10 g of fat/oil containing EPA (eicosapentaenoic acid)/DHA (docosahexaenoic acid) to manufacture a seamless capsule.

INDUSTRIAL APPLICABILITY

According to the present invention, a Java ginger extract having a high content of the phenyl butenoid dimer which exerts an NGF-like action (neuronal process extension action) more effective than NGF can be obtained. Thus, the Java ginger extract of the present invention is useful as a prophylaxis and treatment of neurogenic diseases such as brain ischemia, Alzheimer's disease, Parkinson's disease and Huntington's disease by activating growth, process formation and action of neurocytes. Additionally, Java ginger is widely eaten in Southeast Asia and can be ingested or taken at ease in the form of regular diet daily, as a preventive agent and a therapeutic agent for neurogenic diseases as described above.

In addition, the Java ginger extract composition having a high content of the phenyl butenoid dimer of the present invention is used as a feed for animals such as pets and livestock. The feed can treat the recent phenomena of increased pet neuroses accompanied with the effects of aging and also without increase of the burden on feeders.

The invention claimed is:
1. A Java ginger extract prepared by a method comprising solid-liquid extraction, solid-liquid separation after the extraction, and concentrating the separated liquid; wherein
 (a) a feed for the extraction is Java ginger in unchanged or size-reduced form;
 (b) a solvent for the extraction comprises at least one hydrophilic solvent selected from the group consisting of alcohols having from one to four carbons, dioxane and mixture thereof; and
 (c) a solute of the Java ginger extract comprises a phenyl butenoid dimer (D) represented by the formula (1) and a phenyl butenoid monomer (M) represented by the formula (2);

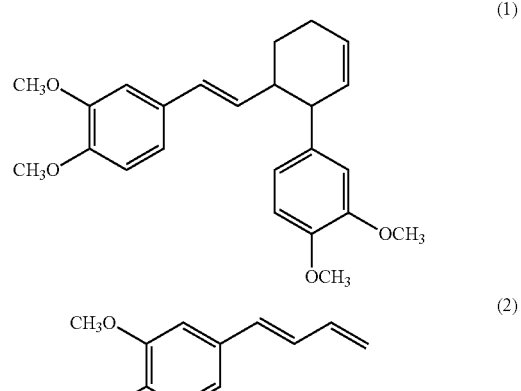

wherein the method further comprises heating at a preset temperature between 55° C. and 160° C. at least one of the feed for extraction, the feed in the solvent, the separated liquid after extraction or a concentrate of said separated liquid; and wherein the produced Java ginger extract comprises D/M ratio of at least 0.6 as represented by the ratio of peak areas measured by a high performance liquid chromatography for the phenyl butenoid dimer (D) and the phenyl butenoid monomer (M).

2. The Java ginger extract according to claim 1, wherein the D/M ratio is at least 1.0.

3. The Java ginger extract according to claim 1, wherein the D/M ratio is at least 5.0.

4. A Java ginger extract composition comprising the Java ginger extract according to claim 1 and a carbohydrate, wherein the composition is in form of powder.

5. A diet food or drink comprising the Java ginger extract composition according to claim 4.

6. A capsule enveloping a liquid comprising the Java ginger extract according to claim 1 and at least one fat or oil component comprising eicosapentaenoic acid or docosahexaenoic acid.

7. A method for manufacturing a Java ginger extract comprising solid-liquid extraction, solid-liquid separation after the extraction, and concentrating the separated liquid; wherein
(a) a feed for the extraction is Java ginger in unchanged or size-reduced form,
(b) a solvent for the extraction comprises at least one hydrophilic solvent selected from the group consisting of alcohols having from one to four carbons, dioxane and mixture thereof;
(c) a solute of the Java ginger extract comprises a phenyl butenoid dimer (D) represented by the formula (1) and a phenyl butenoid monomer (M) represented by the formula (2):

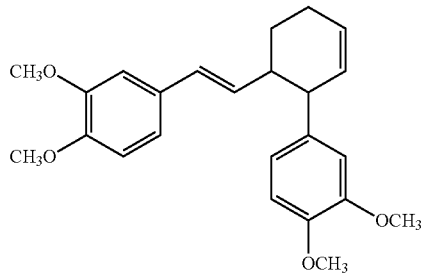

(1)

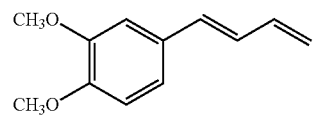

(2)

wherein the method further comprises heating at a preset temperature between 55° C. and 160° C. at least one of the feed for extraction, the feed in the solvent, the separated liquid after extraction or a concentrate of said separate liquid; and wherein the produced Java ginger extract comprises D/M ratio of at least 0.6 as represented by the ratio of peak areas measured by a high performance liquid chromatography for the phenyl butenoid dimer (D) and the phenyl butenoid monomer (M).

8. A Java ginger extract composition comprising the Java ginger extract according to claim 2 and a carbohydrate, wherein the composition is in form of powder.

9. A Java ginger extract composition comprising the Java ginger extract according to claim 3 and a carbohydrate, wherein the composition is in form of powder.

10. A diet food or drink comprising the Java ginger extract composition according to claim 8.

11. A diet food or drink comprising the Java ginger extract composition according to claim 9.

12. A capsule enveloping a liquid comprising the Java ginger extract according to claim 2 and at least one fat or oil component comprising eicosapentaenoic acid or docosahexaenoic acid.

13. A capsule enveloping a liquid comprising the Java ginger extract according to claim 3 and at least one fat or oil component comprising eicosapentaenoic acid or docosahexaenoic acid.

14. The method for manufacturing the Java ginger extract according to claim 7, wherein the D/M ratio is at least 1.0.

15. The method for manufacturing the Java ginger extract according to claim 7, wherein the D/M ratio is at least 5.0.

* * * * *